United States Patent

Kunihiro et al.

[11] Patent Number: 5,149,540
[45] Date of Patent: Sep. 22, 1992

[54] THROMBIN COMPOSITION FOR ORAL ADMINISTRATION

[75] Inventors: Yasuyuki Kunihiro; Ryo Tanaka; Seishichi Hata; Koji Yamada, all of Shinjuku, Japan

[73] Assignee: Mochida Pharmaceutical Co., Ltd., Tokyo, Japan

[21] Appl. No.: 661,226

[22] Filed: Feb. 27, 1991

[30] Foreign Application Priority Data

Mar. 1, 1990 [JP] Japan .................................. 2-50494

[51] Int. Cl.$^5$ .......................................... A61K 37/547
[52] U.S. Cl. .................................. 424/489; 424/94.1; 424/94.3; 424/94.64; 424/499; 424/529; 514/802; 514/834
[58] Field of Search ................... 424/94.1, 94.3, 94.64, 424/529, 489, 499; 514/802, 834

[56] References Cited

U.S. PATENT DOCUMENTS

| | | | |
|---|---|---|---|
| 2,433,299 | 12/1947 | Seegers | 424/94.3 X |
| 2,558,395 | 6/1951 | Studer | 424/94.64 X |
| 3,515,642 | 6/1970 | Mima et al. | 424/94.3 X |
| 4,297,344 | 10/1981 | Schwinn et al. | 530/381 |
| 4,363,319 | 12/1982 | Altshuler | 424/447 X |
| 4,427,650 | 1/1984 | Stroetmann | 514/802 X |
| 4,563,351 | 1/1986 | Caslavsky et al. | 424/606 |
| 4,696,812 | 9/1987 | Silbering et al. | 424/94.64 X |
| 4,923,815 | 5/1990 | Tanaka et al. | 435/183 |

FOREIGN PATENT DOCUMENTS

| | | | |
|---|---|---|---|
| 0204045 | 10/1986 | European Pat. Off. | 33/48 |
| 2-218618 | 8/1990 | Japan . | |
| 8203871 | 11/1982 | PCT Int'l Appl. | 35/16 |

OTHER PUBLICATIONS

Patent Abstracts of Japan, "Thrombin-Containing Medicinal Composition", Yoshiki Yatsuno, vol. 13, No. 362 (C-625), Aug. 14, 1989.

Primary Examiner—Thurman K. Page
Assistant Examiner—Robert H. Harrison
Attorney, Agent, or Firm—Oliff & Berridge

[57] ABSTRACT

A stable thrombin composition for oral administration having an excellent solubility is prepared with thrombin as a hemostatic ingredient, gelatin, albumin and glycine as a stabilizer and sucrose and/or sugar alcohol as a carrier. The thrombin composition is effective for the treatment of hemorrhage in the upper alimentary canal, is stable even at room temperature conditions for long periods of time, has excellent solubility and can be orally administered in a simple manner.

16 Claims, No Drawings

THROMBIN COMPOSITION FOR ORAL ADMINISTRATION

BACKGROUND OF THE INVENTION

1. Field of the Invention

The present invention relates to a stable thrombin composition formulated for oral administration which is used for treating hemorrhage in the upper alimentary canal, is stable even at room temperature for long periods of time, has excellent solubility and can be administered orally in a simple manner.

2. Description of the Prior Art

Thrombin is a blood coagulation factor which is well-known and acts directly on fibrinogen to convert it into fibrin in the final stages of blood coagulation. When fibrinogen is present in blood, blood localized at the place of hemorrhage is rapidly coagulated to clot the end of an injured blood vessel. The blood clot mass contracts in the presence of platelets so that the end of the blood vessel is sealed and bleeding stops completely.

Thrombin is prepared by combining thromboplastin with prothrombin prepared from human or bovine blood in the presence of calcium ions. A thrombin composition has been hitherto prepared by filling a vial with a solution of the composition and freeze drying.

Conventional thrombin compositions should be stored below 10° C., because storage at room temperature results in a decrease in physiological activity (The Pharmacopeia of JAPAN, 11th Edition). When this composition is used, it is generally administered either by spraying a solution of the composition in isotonic sodium chloride solution (50 to 1000 units of thrombin per milliliter) or by withdrawing the content from the vial and sprinkling the powder onto the area of bleeding. (The "unit" is defined by NIH.)

Where the composition is used to treat bleeding in the upper alimentary canal, the composition is dissolved in a suitable buffer solution in 200 to 400 units of thrombin per milliliter and the resulting solution is orally administered.

As stated above, however, where the thrombin composition is used to treat the upper alimentary canal, it is administered several times a day at intervals of a few hours. Therefore, it is desirable to develop a composition which can be orally administered by the patient himself in a simple manner.

For this purpose, it is necessary to develop a composition in which the thrombin is stable even when stored at room temperature, even though the composition is not contained in a sealed container such as a vial.

In addition, most vial preparations are used for injection, and that there is a danger that the thrombin composition prepared in a vial might be injected by an inadvertent error in medical institutions. In order to avoid this danger, care such as marking the vial with a special label, has been taken. If no vial were used, however, this special care would be unnecessary. Furthermore, the thrombin composition in a vial has problems in that it is inconvenient for the patient to carry the vial, and handling it is complicated because the vial should be stored below 10° C.

Thrombin compositions for the treatment of hemorrhage in the alimentary canal which permit oral administration in a simple manner are disclosed as prior art in Japanese Patent Application Laid-Open Nos. Hei 1-93536 and Hei 1-121224. The former composition is characterized by enteric coated preparations, and the latter is characterized by containing an alkaline substance to prevent inactivation of thrombin in the stomach. With respect to stability of thrombin compositions during storage, however, these references disclose its stability in a cold place for only 21 days, but fail to disclose any stability at room temperature conditions.

SUMMARY OF THE INVENTION

Accordingly, an object of the present invention is to provide a stable thrombin composition for oral administration which is useful for the treatment of hemorrhage in the upper alimentary canal, has excellent solubility, can be orally administered in a simple manner and is stable even at room temperature conditions.

As a result of extensive investigations, the present inventors have found that by using thrombin as a hemostatic ingredient in combination with a specific, pharmaceutically acceptable stabilizer and carrier, a stable thrombin composition for oral administration can be prepared which has excellent solubility, can be orally administered in a simple manner and is stable even at room temperature conditions for long periods of time. The present invention accomplishes these objects by providing a stable thrombin composition for oral administration comprising thrombin as a hemostatic ingredient and a specific, pharmaceutically acceptable stabilizer and carrier, which has excellent solubility.

DETAILED DESCRIPTION OF PREFERRED EMBODIMENTS

Any thrombin having physiological activity can be used in the present invention. In general, thrombin prepared by combining calcium salts and thromboplastin with prothrombin extracted and purified from bovine or human plasma can be used. In addition, thrombin may also be used in the form of freeze-dried powders or in a highly concentrated solution.

Conventional thrombin compositions have been prepared in vials but these compositions have the foregoing problems, particularly when used for oral administration.

In order to solve these problems, the thrombin compositions of the present invention may be in the form of powders, fine granules, granules, tablets, etc., desirably powders, fine granules or granules.

The thrombin composition of the present invention for oral administration may be prepared with specific, pharmaceutically acceptable stabilizers and carriers Stabilizers which may be used in the present invention are gelatin, albumin, glycine, etc., preferably gelatin or glycine. There is no particular limitation to gelatin used in the present invention, as long as it is prepared by treating bones, skins, ligaments or tendons of animal with an acid or an alkali, extracting the resulting collagent with water while heating, drying the extract under reduced pressure and drying the resulting gel. The amount of stabilizer is from 5 to 100 mg, preferably from 10 to 50 mg, per 10,000 units of thrombin.

Carriers which may be used are sucrose or sugar alcohol, preferably sucrose, D-mannitol, etc., more preferably sucrose.

The reasons why sucrose or sugar alcohol is used as the carrier are as follows. Firstly, in a case that the compositions of the present invention are prepared, when the drying step involves heating over a long period of time, the activity of thrombin decreases. Thus, a carrier which does not require drying for a long period of time is necessary. Where the carrier of the present invention is used, granulation can be accomplished at a low moisture content so that the drying time is shortened.

The second reason is to provide a carrier having an excellent solubility in water and which is free of precipitates. That is, when used to treat a hemorrhage in the upper alimentary canal, the present composition is dissolved in a suitable solvent, for example, buffer solution, milk, isotonic sodium chloride solution or distilled water and that solution is used for the treatment. In this case, if some substance is not dissolved but remains as a precipitate, the physiologically active ingredient is adsorbed onto the insoluble substance so that sufficient pharmaceutical effects cannot be expected or the physical disorder remains even after administration of the composition.

The amount of sucrose or sugar alcohol which is used as the carrier herein is 0.1 to 2 g, preferably 0.5 to 1 g, per 10,000 units of thrombin.

When the present composition is used to treat a hemorrhage in the upper alimentary canal, the composition is dissolved in a suitable solvent as described above, for example, buffer solution, milk, isotonic sodium chloride solution or distilled water and the solution is administered in a concentration of 50 to 1000 units of thrombin per milliliter. In this case, an antacid may also be used in combination, if necessary and desired.

The composition of the present invention can maintain the thrombin activity over a long period of time even at room temperature and has excellent stability. Where the present composition is dissolved in a suitable solvent, for example, buffer solution, milk, isotonic sodium chloride solution or distilled water, the composition is dissolved within a minute and no precipitate is observed. Furthermore, the thrombin activity in the solution does not decrease within 24 hours.

Hereinafter the composition is described specifically with reference to test examples and the test results of the present invention are described below.

TEST EXAMPLE 1

Experiment on the effect of stabilizer

About 1 g of the composition prepared in Example 1 or Reference Example 1 later described is put in a sealed container. The container is allowed to stand under severe conditions at 60° C. over a range of time from 7 days to 2 months. During this period, the decrease in the thrombin activity of each composition is determined to compare the stability of the thrombin in the presence or absence of the stabilizer.

The thrombin activity is determined by a modified method of The Pharmacopeia of JAPAN, 11th Edition. The value of thrombin activity before the composition is allowed to stand is 100 and a value of the thrombin activity is determined after it has been allowed to stand for the stated period of time.

The results are shown in Table 1.

TABLE 1

| Composition | Period | | | |
|---|---|---|---|---|
| Tested | 7 Days | 14 Days | 1 Month | 2 Months |
| Example 1 | 93 | 87 | 79 | 78 |
| Reference Example 1 | 83 | 61 | 54 | 37 |

The numerical values show the thrombin activity after being allowed to stand, when the thrombin activity before being allowed to stand is 100.

As is clear from Table 1, the composition of the present invention shows a marked stabilized effect by the addition of the stabilizer in the present invention, even when it is stored at a high temperature.

TEST EXAMPLE 2

Experiment on stability under storage over long period of time

About 1 g of the composition prepared in Example 2 later described is placed in a bag composed of a sheet prepared by laminating an aluminum foil with cellophane and plastic and the bag is sealed with heating. The bag is stored under conditions at 40° C. ($\pm 1°$ C.), relative humidity of 75% ($\pm 5\%$) and under room temperature conditions for 1 to 6 months, based on the acceleration test standards given by Drug approval and licensing Procedures in JAPAN. During this period, the thrombin activity of the composition is determined.

Determination of the thrombin activity is performed as in Test Example 1.

The results are shown in Table 2.

TABLE 2

| Composition Tested | Conditions for Storage | Period | | | |
|---|---|---|---|---|---|
| | | 1 Month | 2 Months | 3 Months | 6 Months |
| Example 2 | 40° C., 75% | 101 | 99 | 97 | 99 |
| | room temperature | 99 | 102 | 98 | 101 |

The numerical values show the thrombin activity after being allowed to stand, when the thrombin activity before being allowed to stand is 100.

As is clear from Table 2, the composition of the present invention is stable even under conditions at 40° C. ($\pm 1°$ C.) and relative humidity of 75% ($\pm 5\%$) over 6 months. The composition has excellent stability and from the foregoing results it can be assumed to be stable for at least 3 years at room temperature.

TEST EXAMPLE 3

Solubility of the composition and stability in a solution state

About 1 g each of the composition prepared in Example 2 later described is placed in each beaker of 100 ml and 50 ml each of distilled water, isotonic sodium chloride solution, phosphate buffer solution and milk are added thereto, respectively. When mildly stirred, a time period for dissolution (i.e., the period of time until the presence of powder is not noted at the bottom of the beaker) and properties of the resulting solution are observed.

Furthermore, these solutions are allowed to stand at room temperature and the thrombin activity in each solution is measured up to 24 hours.

Determination of the thrombin activity is performed as in Test Example 1.

The results are shown in Table 3.

TABLE 3

| Solvents | Time for Dissolution and Properties of Solution | 6 Hours After | 24 Hours After |
|---|---|---|---|
| Distilled water | The composition was dissolved within a minute; no precipitate | 99 | 99 |

TABLE 3-continued

| Solvents | Time for Dissolution and Properties of Solution | 6 Hours After | 24 Hours After |
| --- | --- | --- | --- |
| | was observed | | |
| Isotonic sodium chloride solution | The composition was dissolved within a minute; no precipitate was observed | 98 | 101 |
| Phosphate buffer solution | The composition was dissolved within a minute; no precipitate was observed | 100 | 101 |
| Milk | The composition was dissolved within a minute; no precipitate was observed | 103 | 102 |

The numerical values show the thrombin activity after being allowed to stand, when the thrombin activity before being allowed to stand is 100.

As is clear from Table 3, the solubility of the composition of the present invention is extremely high and no insoluble precipitates are noted. The composition of the present invention is excellent for oral administration. In addition, the thrombin activity in the solutions in which the composition is dissolved is stable over long periods of time and the composition is useful.

EXAMPLES

Next, the present invention is described with reference to the examples and reference example but is not deemed to be limited to these examples.

In the examples, a solution of thrombin prepared by combining calcium salt and thromboplastin with prothrombin extracted and purified from bovine serum is prepared with a specific activity of 1000 units/mg protein in a concentration of 10,000 units/ml and is used.

EXAMPLE 1

| Thrombin | 20,000,000 units |
| --- | --- |
| Glycine | 30 g |
| Gelatin | 20 g |
| Sucrose | appropriate amount |
| Total | 1,000 g |

Glycine is added to a thrombin solution and dissolved. By freeze drying, a powder is obtained. Sucrose is added to the resulting powder. The mixture is mixed and stirred. With mixing and stirring, a solution of gelatin in distilled water is sprayed onto the mixture to give granules. After drying with a drier under heating, the granules are sieved to give fine granules.

EXAMPLE 2

| Thrombin | 20,000,000 units |
| --- | --- |
| D-Mannitol | 30 g |
| Gelatin | 20 g |
| Sucrose | appropriate amount |
| Total | 1,000 g |

D-Mannitol is added to a thrombin solution and dissolved. By freeze drying, a powder is obtained. Sucrose is added to the resulting powder. The mixture is mixed and stirred. With mixing and stirring, a solution of gelatin in distilled water is sprayed onto the mixture to give granules. After drying with a drier under heating, the granules are sieved to give fine granules.

REFERENCE EXAMPLE 1

| Thrombin | 20,000,000 units |
| --- | --- |
| Sucrose | appropriate amount |
| Total | 1,000 g |

A thrombin solution is freeze dried to give a powder. Sucrose is added to the resulting powder. The mixture is mixed and stirred. With mixing and stirring, distilled water is sprayed onto the mixture to give granules. After drying with a drier under heating, the granules are sieved to give fine granules.

While the invention has been described in detail and with reference to specific embodiments thereof, it is apparent to one skilled in the art that various changes and modifications can be made therein without departing from the spirit and the scope of the present invention.

What is claimed is:

1. A hemostatically solid composition comprising:
   a hemostatically effective amount of thrombin as an active ingredient;
   0.9 to 9.0 wt % of at least one stabilizer selected from the group consisting of gelatin, albumin and glycine; and
   more than 89.0 to 99.0 wt % of at least one carrier selected from the group consisting of sucrose and mannitol.

2. The composition of claim 1, wherein said stabilizer is gelatin.

3. The composition of claim 1, wherein said composition is in the form of granules, fine granules or powders.

4. The composition of claim 1, wherein the composition is in a form suitable for oral administration.

5. The composition of claim 1, further comprising a solvent.

6. The composition of claim 5, wherein said solvent is selected from the group consisting of buffer solution, milk, isotonic sodium chloride solution, and distilled water.

7. The composition of claim 5, containing 50 to 1000 units of said thrombin per milliliter of said solvent.

8. The composition of claim 6, containing 200 to 400 units of said thrombin per milliliter of said buffer solution.

9. The composition of claim 1, said composition being stable for from 1 month to 6 months at room temperature and relative humidity of from 70-80%.

10. A method of treating hemorrhage by administration of a hemostatically solid composition comprising:
    a hemostatically effective amount of thrombin as an active ingredient;
    0.1 to 9.0 wt % of at least one stabilizer selected from the group consisting of gelatin, albumin and glycine; and
    more than 90.0 wt % of at least one carrier selected from the group consisting of sucrose and mannitol.

11. The method of claim 10, wherein said hemorrhage is in the upper alimentary canal.

12. The method of claim 10, wherein said stabilizer is gelatin.

13. The method of claim 10, wherein said composition is in the form of granules, fine granules or powders.

14. The method of claim 10, wherein the composition is administered orally.

15. The composition of claim 1, wherein said carrier is sucrose.

16. The composition of claim 1, further comprising a potable solvent in which the composition is dissolved to be in a form suitable for use in oral administration.

* * * * *